(12) United States Patent
Atis et al.

(10) Patent No.: US 6,503,521 B1
(45) Date of Patent: Jan. 7, 2003

(54) FIBER-CONTAINING BASE COMPOSITION FOR USE WITH MASCARA

(75) Inventors: Balanda Atis, Clark, NJ (US); Mohamed Kanji, Clark, NJ (US); Carl Orr, Clark, NJ (US)

(73) Assignee: L'Oréal S.A., Paris (FR)

( * ) Notice: Subject to any disclaimer, the term of this patent is extended or adjusted under 35 U.S.C. 154(b) by 8 days.

(21) Appl. No.: 09/717,269

(22) Filed: Nov. 22, 2000

(51) Int. Cl.$^7$ .............................. A61K 7/06; A61K 6/00; A61K 7/00
(52) U.S. Cl. ....................................... 424/401; 424/70.1
(58) Field of Search ................................. 424/70.1, 401

(56) References Cited

U.S. PATENT DOCUMENTS 5,534,247 A * 7/1996 Franjac et al. ............... 424/707

FOREIGN PATENT DOCUMENTS

| JP | 57-158714 | | 9/1982 |
|---|---|---|---|
| JP | 7-267827 | | 10/1995 |
| JP | 7-267828 | * | 10/1995 |
| JP | 10-291917 | | 11/1998 |

* cited by examiner

*Primary Examiner*—Thurman K. Page
*Assistant Examiner*—S. Howard
(74) *Attorney, Agent, or Firm*—Finnegan, Henderson, Farabow, Garrett & Dunner, L.L.P.

(57) ABSTRACT

A cosmetic composition, particularly useful as a base composition for mascara, containing fibers and at least three film formers: at least one tacky film former soluble or dispersible in water; at least one tacky film former soluble in oil; and at least one additional water-soluble or water-dispersible film former. The invention also relates to a method for pretreating eyelashes prior to application of mascara and a method for providing volume and length to eyelashes using the inventive composition.

24 Claims, No Drawings

FIBER-CONTAINING BASE COMPOSITION FOR USE WITH MASCARA

The present invention is directed to compositions containing fibers and at least three film formers: at least one tacky film former soluble or dispersible in water; at least one tacky film former soluble in oil; and at least one additional film former soluble or dispersible in water. The invention can be useful as a base composition for pre-treating eyelashes prior to application of mascara. When used under any typical mascara composition, the inventive base composition may provide volume or length to eyelashes.

The use of fibers in mascara compositions to lengthen or volumize eyelashes is known in the art. However, the inclusion of fibers in these compositions has presented various possible difficulties. Primary among the possible drawbacks of fiber use has been undesirable flaking and detachment of the fibers from the eyelashes due to the insufficient adhesive properties of the film formers in the mascara. Such flaking also made it difficult to apply more than one coat of mascara, as the application of subsequent coats was found to further act to detach fibers from the lashes.

Accordingly, there existed a desire in the art to find a way to use fibers to obtain enhanced volume and/or length for eyelashes without the disadvantages of flaking and detachment of the fibers. It was also desired to use fibers but also obtain ease of application. Development of such compositions involves a difficult balance, as the tackiness of film formers used in a fiber-containing cosmetic composition, particularly for use on eyelashes, must be enough to prevent the fibers from flaking off over time, but not so tacky that the composition is not easily removable from the eyelashes and is sticky and uncomfortable.

The present invention addresses these issues. Accordingly, the present invention, in one aspect, provides a cosmetic composition comprising at least one tacky film former soluble or dispersible in water; at least one tacky film former soluble in oil; at least one additional film former soluble or dispersible in water; and fibers. When the inventive composition is used as a base composition for mascara, the combination of tacky film formers can, in at least some embodiments, allow the fibers applied in the base composition to remain intact on the eyelashes without flaking when the mascara is applied on top of the base. The combination of tacky film formers can, in at least some embodiments, also provide enough tackiness to allow the mascara to stick to the base when the mascara is applied on top of the base.

In another aspect, the invention also relates to a method for pre-treating eyelashes prior to application of mascara by applying to the eyelashes a fiber-containing composition as described above. In yet another aspect, the invention is drawn to a method for providing volume and/or length to eyelashes by first applying to the eyelashes a fiber-containing base composition as described above and then applying a mascara composition to the eyelashes directly on top of the base composition. In at least certain embodiments of the invention, the need for multiple applications of mascara to achieve volume and length is eliminated.

It is to be understood that both the foregoing general description and the following detailed description are exemplary and explanatory only and are not restrictive of the invention as claimed.

Reference will now be made in detail to exemplary embodiments of the present invention. The invention, in one aspect, provides a cosmetic composition comprising at least one tacky film former soluble or dispersible in water; at least one tacky film former soluble in oil; at least one additional film former soluble or dispersible in water; and fibers. The composition of the invention can be used as a base composition for mascara. The fibers in the composition may act to provide length and/or volume to the eyelashes but also can be stable on the eyelashes such that when the mascara is applied on top of the base, the fibers stay on the eyelashes. The instantaneous results after mascara application may include visibly longer, thicker lashes. The composition of the invention may also be easy to apply, easy to remove, water-resistant and comfortable to wear. For purposes of this invention, "tacky" is defined as sticky or adhesive to the touch.

Also, for purposes of this invention, the term "soluble or dispersible in water" means that the substance in question will not precipitate out or coagulate, i.e., that it dissolves up to the limit of saturation. The term "soluble in oil" means "miscible in oil"; in other words, if a substance is not soluble in oil, it is immiscible, forming distinct layering in the oil phase, an indication that the substance is not compatible or soluble in the oil phase.

The at least one tacky film former soluble or dispersible in water is chosen from polyvinyl alcohol, polyvinyl acetates (such as FULATEX (R) sold by H. B. Fuller Co.), vinylpyrrolidone/acrylates/lauryl methacrylate copolymer (such as STYLEZE 2000 sold by ISP), acrylates/$C_{1-2}$ succinates/hydroxyacrylates copolymer (such as ALLIANZ LT-120 sold by ISP), PVP/DMAPA acrylates copolymer (such as STYLEZE CC-10 sold by ISP) cellulose acetate phthalate aqueous dispersion (such as AQUACOAT CPD sold by FMC Corp.), and crosslinked poly (2-ethylhexyl acrylate) in water (such as GEL-TAC 100 series sold by API). In one embodiment, the at least one tacky film former soluble or dispersible in water is polyvinyl alcohol. Polyvinyl alcohol is available, for example, from Air Products in different hydrolysis grades under the tradename AIRVOL. The at least one tacky film former soluble or dispersible in water may be present in the composition in an amount ranging from 0.5% to 25% relative to the total weight of the composition. In another embodiment, the at least one tacky film former soluble or dispersible in water may be present in an amount ranging from 1% to 15%, relative to the total weight of the composition. In still another embodiment, the at least one tacky film former soluble or dispersible in water may be present in an amount ranging from 1% to 10%, relative to the total weight of the composition.

The at least one tacky film former soluble in oil is chosen from hydrogenated polyisobutenes, adipic acid/diethylene glycol/glycerin crosspolymers (such as that sold as LEX-OREZ 100 by Inolex), polyethylenes, polyvinyl laurates, and synthetic terpene based resins (such as PICCOLYTE A115 and C115, sold by Hercules). In one embodiment, the at least one oil-soluble tacky film former is chosen from hydrogenated polyisobutenes. Hydrogenated polyisobutenes are available from, for example, Collaborative Laboratories, East Setauket, N.Y., under the name POLYSYNLANE. In one embodiment, the hydrogenated polyisobutenes to be used in the claimed invention have a weight average molecular weight of greater than 1500. In another embodiment, the hydrogenated polyisobutenes have a weight average molecular weight greater than 2000 and in yet another embodiment, greater than 3000. The at least one tacky film former soluble in oil may, for example, be present in the composition in an amount ranging from 1% to 45%, relative to the total weight of the composition. In one embodiment, the at least one tacky film former soluble in oil is present in the composition in an amount ranging from 3% to 30%, relative to the total weight of the composition. In yet another embodiment, the at least one tacky film former soluble in oil may be present in the composition in an amount ranging from 3% to 20%, relative to the total weight of the composition.

The at least one additional film former is chosen from the list of film formers set forth on pages 1744–1747 of the CTFA International Cosmetic Ingredient Dictionary, 8$^{th}$ edition (2000), and is different from the at least one tacky film former soluble or dispersible in water and the at least one tacky film former soluble in oil discussed above. In one embodiment, the at least one additional film former is polyvinylpyrrolidone. Polyvinylpyrrolidone is available from, for example, ISP in different viscosity grades under the tradenames PVP K. The at least one additional film former may, for example, be present in the composition in an amount ranging from 0.1% to 10% relative to the total weight of the composition. In a further embodiment, the at least one additional film former is present in an amount ranging from 1% to 6% relative to the total weight of the composition.

The fibers useful in the present invention may be chosen from natural and synthetic fibers. Natural fibers include, but are not limited to cotton, silk, wool, and other keratin fibers. Synthetic fibers include, but are not limited to, polyester, rayon, nylon and other polyamide fibers. The fibers may, for example, be present in the composition in an amount ranging from 0.5% to 10% relative to the total weight of the composition. In a further embodiment, the fibers are present in an amount ranging from 1% to 5% relative to the total weight of the composition. In one embodiment, the fibers may, for example, have an average length ranging from 0.5 mm to 4.0 mm, such as from 1.5 mm to 2.5 mm.

It is also possible to add to the composition of the invention any additives customarily used in cosmetic compositions, such as: thickening agents, preservatives, UV-screening agents, pigments, fillers, polymer resins, volatile solvents, and waxes.

Not to be limited by theory, the inventors have discovered that, in one embodiment, the inventive composition may be in the form of an oil-in-water emulsion. In such an emulsion, it is advantageous to have a tacky film former in each of the aqueous (external) and oil (internal) phases of the emulsion. Accordingly, in this embodiment, the aqueous phase of the emulsion contains the at least one tacky film former soluble or dispersible in water and the at least one additional film former and the oil phase contains the at least one tacky film former soluble in oil.

The present invention also provides for a method for pre-treating eyelashes prior to application of mascara by applying to the eyelashes a composition as described above. The tacky film formers work together to help the fibers sufficiently adhere to the eyelashes so that when the mascara is applied on top of the inventive base composition, the fibers remain on the lashes. When only one of the required tacky film formers is present, the adherence of the fibers on the lashes is lessened.

The present invention also relates to a method for providing volume and/or length to eyelashes by applying to the eyelashes a base composition as described above and then applying a mascara composition to the eyelashes directly on top of the base composition. Thus, the base compositions of the invention may be used to control the volume and extending or lengthening effect of mascara on eyelashes.

The invention will be illustrated by, but is not intended to be limited to, the following example.

EXAMPLE 1

A mascara base composition containing the following ingredients was prepared as set forth below:

| PHASE | Ingredient | w/w % |
|---|---|---|
| A | Deionized water | 56.65 |
|   | Polyvinylpyrrolidone (PVP K-30 from ISP) | 1.00 |
|   | Preservatives | 0.20 |
|   | Triethanolamine | 2.50 |
|   | Humectant | 1.00 |
|   | Defoaming agent | 0.10 |
|   | Chelating agent | 0.20 |
|   | Polyvinyl Alcohol (AIRVOL 540) | 3.50 |
| B | Waxes | 5.85 |
|   | Emulsifiers | 4.70 |
|   | Hydrogenated Polyisobutene (Polysynlane SV ®) | 15.00 |
| C | Rayon Flock Fiber | 3.00 |
| D | Preservatives | 1.10 |
| E | Sodium Dehydroacetate | 0.20 |
| F | SD 40 Alcohol | 5.00 |

Procedure for Preparation

The deionized water and PVP K-30 were mixed while heating to 80 to 85° C. and the remaining ingredients of phase A were added while still heating to 80 to 85° C. In a separate vessel, the Polysylane SV was heated to 85° C. While maintaining the temperature at 85° C., the remaining ingredients of phase B were added to the Polysylane SV. Phase B was then added to Phase A, still at 85° C. The mixture was homogenized for 20 minutes at 80 to 85° C. The batch was cooled to 70° C. and phase C was slowly added. Phase D was added at 45° C. Phase E was added at 40° C. Phase F was added at 30° C.

Results

The prepared mascara base composition was applied to eyelashes and found to increase their volume and length when a regular mascara composition was applied on top of the base. The fibers stayed on the lashes even with application of the top coat.

EXAMPLE 2

Five (5) subjects were tested to compare the effects of mascara applied directly to eyelashes versus mascara applied to eyelashes to which the inventive fiber-containing base composition had been applied. An aesthetician applied mascara without a base composition to the eyelashes of one eye of each subject. The same mascara was then applied to the eyelashes of the other eye of each subject, to which the inventive base composition had been applied. The results were rated on a scale of 0 to 5.0, with 5.0 being the best. Tables 1 and 2 below show the results for each of the five panelists for lengthening and thickening (volume) of lashes, respectively.

TABLE 1

| | Lengthening of Lashes | |
|---|---|---|
| PANELIST | MASCARA ALONE | BASE + MASCARA |
| #1 | 4.0 | 5.0 |
| #2 | 4.0 | 5.0 |
| #3 | 5.0 | 3.5 |
| #4 | 5.0 | 5.0 |
| #5 | 3.5 | 5.0 |

TABLE 2

Thickening of Lashes

| PANELIST | MASCARA ALONE | BASE + MASCARA |
|---|---|---|
| #1 | 4.0 | 5.0 |
| #2 | 4.0 | 5.0 |
| #3 | 4.0 | 3.0 |
| #4 | 4.5 | 5.0 |
| #5 | 3.5 | 5.0 |

As can be seen in Table 1, three of the five panelists found the inventive base composition+mascara combination to result in longer lashes than the mascara alone. One panelist saw no change, and one panelist rated the inventive combination lower. Table 2 shows that four of the five panelists found the inventive base composition+mascara combination to result in thicker lashes. The same panelist as above, #3, rated the inventive combination lower. Thus, overall, the inventive combination was found to give thicker and longer lashes than mascara alone.

It will be apparent to those skilled in the art that various modifications and variations can be made in the compositions and methods of the present invention without departing from the spirit or scope of the invention. Thus, it is intended that the present description cover the modifications and variations of this invention provided that they come within the scope of the appended claims and their equivalents.

What is claimed is:

1. A cosmetic composition comprising:
   at least one tacky film former soluble or dispersible in water;
   at least one tacky film former soluble in oil;
   at least one additional film former soluble or dispersible in water; and fibers.

2. A cosmetic composition according to claim 1, wherein said at least one tacky film former soluble or dispersible in water is chosen from polyvinyl alcohol, polyvinyl acetates, vinylpyrrolidone/acrylates/lauryl methacrylate copolymer, acrylates/$C_{1-2}$ succinates/hydroxyacrylates copolymer, PVP/DMAPA acrylates copolymer, cellulose acetate phthalate aqueous dispersion, and crosslinked poly (2-ethylhexyl acrylate).

3. A cosmetic composition according to claim 2, wherein said at least one tacky film former soluble or dispersible in water is polyvinyl alcohol.

4. A cosmetic composition according to claim 1, wherein said at least one tacky film former soluble or dispersible in water is present in the composition in an amount ranging from 0.5% to 25% relative to the total weight of the composition.

5. A cosmetic composition according to claim 4, wherein said at least one tacky film former soluble or dispersible in water is present in the composition in an amount ranging from 1% to 15%, relative to the total weight of the composition.

6. A cosmetic composition according to claim 5, wherein said at least one tacky film former soluble or dispersible in water is present in the composition in an amount ranging from 1% to 10%, relative to the total weight of the composition.

7. A cosmetic composition according to claim 1, wherein said at least one tacky film former soluble in oil is chosen from hydrogenated polyisobutenes, adipic acid/diethylene glycol/glycerin crosspolymer, polyethylene, polyvinyl laurate, and synthetic terpene based resins.

8. A cosmetic composition according to claim 7, wherein said at least one tacky film former soluble in oil is a hydrogenated polyisobutene.

9. A cosmetic composition according to claim 1, wherein said at least one tacky film former soluble in oil is present in the composition in an amount ranging from 1% to 45% relative to the total weight of the composition.

10. A cosmetic composition according to claim 9, wherein said at least one tacky film former soluble in oil is present in the composition in an amount ranging from 3% to 30% relative to the total weight of the composition.

11. A cosmetic composition according to claim 10, wherein said at least one tacky film former soluble in oil is present in the composition in an amount ranging from 3% to 20% relative to the total weight of the composition.

12. A cosmetic composition according to claim 1, wherein said at least one additional film former is polyvinylpyrrolidone.

13. A cosmetic composition according to claim 1, wherein said at least one additional film former is present in the composition in an amount ranging from 0.1% to 10% relative to the total weight of the composition.

14. A cosmetic composition according to claim 13, wherein said at least one additional film former is present in the composition in an amount ranging from 1% to 6% relative to the total weight of the composition.

15. A cosmetic composition according to claim 1, wherein said fibers are chosen from natural and synthetic fibers.

16. A cosmetic composition according to claim 15, wherein said natural fibers are chosen from cotton, silk, wool, and other keratin fibers.

17. A cosmetic composition according to claim 15, wherein said synthetic fibers are chosen from polyester, rayon, nylon and other polyamide fibers.

18. A cosmetic composition according to claim 15, wherein said fibers have an average length ranging from 0.5 mm to 4.0 mm.

19. A cosmetic composition according to claim 18, wherein said fibers have an average length ranging from 1.5 mm to 2.5 mm.

20. A cosmetic composition according to claim 15, wherein said fibers are present in the composition in an amount ranging from 0.5% to 10% relative to the total weight of the composition.

21. A cosmetic composition according to claim 20, wherein said fibers are present in the composition in an amount ranging from 1% to 5% relative to the total weight of the composition.

22. A cosmetic composition according to claim 1, wherein said composition is in the form of an oil-in-water emulsion having an aqueous phase and an oil phase,
   wherein the aqueous phase contains said at least one tacky film former soluble or dispersible in water and said at least one additional film former soluble or dispersible in water and
   said oil phase contains said at least one tacky film former soluble in oil.

23. A method for pre-treating eyelashes prior to application of mascara, said method comprising applying to the eyelashes a composition comprising
   at least one tacky film former soluble or dispersible in water;
   at least one tacky film former soluble in oil;
   at least one additional film former soluble or dispersible in water; and fibers.

24. A method for providing volume and/or length to eyelashes comprising applying to the eyelashes a base composition comprising
- at least one tacky film former soluble or dispersible in water;
- at least one tacky film former soluble in oil;
- at least one additional film former soluble or dispersible in water; and fibers, and applying a mascara composition to the eyelashes directly on top of said base composition.

* * * * *